United States Patent [19]

Senaratne

[11] Patent Number: 4,629,808

[45] Date of Patent: Dec. 16, 1986

[54] PROCESS FOR HYDROLYZING NITRILES

[75] Inventor: K. Pushpananda A. Senaratne, Baton Rouge, La.

[73] Assignee: Ethyl Corporation, Richmond, Va.

[21] Appl. No.: 746,768

[22] Filed: Jun. 20, 1985

[51] Int. Cl.$^4$ .............................................. C07C 63/34
[52] U.S. Cl. ................................. 562/467; 560/100; 562/490
[58] Field of Search ................ 562/490, 467; 560/100

[56] References Cited

U.S. PATENT DOCUMENTS

| | | | |
|---|---|---|---|
| 2,361,576 | 10/1944 | Tomlinson, Jr. | 562/490 |
| 4,174,452 | 11/1979 | Gelbein et al. | 562/490 |
| 4,214,087 | 7/1980 | Fanelli et al. | 562/490 |
| 4,560,794 | 12/1985 | Foster | 562/467 |
| 4,562,286 | 12/1985 | Foster | 562/467 |
| 4,590,010 | 5/1986 | Ramachandran | 562/467 |

Primary Examiner—Paul J. Killos
Attorney, Agent, or Firm—Donald L. Johnson; John F. Sieberth; Patricia J. Hogan

[57] ABSTRACT

A 6-alkoxy-5-trifluoromethyl-1-cyanonaphthalene is hydrolyzed to the corresponding acid in high yield by reacting it with an aqueous alcoholic base under moderate pressure at a temperature of about 115°–130° C. A preferred nitrile is 6-methoxy-5-trifluoromethyl-1-cyanonaphthalene, preferred bases are sodium and potassium hydroxides, utilizable alcohols are alkanols containing 1–3 carbons, and preferred pressures are in the range of about 90–110 psi.

10 Claims, No Drawings

PROCESS FOR HYDROLYZING NITRILES

FIELD OF INVENTION

This invention relates to 6-alkoxy-5-trifluoromethyl-1-naphthoic acids and more particularly to a process for preparing them.

BACKGROUND

As disclosed in copending application Ser. No. 724,474, filed Apr. 18, 1985, in the names of Ramachandran, Davidson, and Maloney (Ramachandran et al.), it is known that 6-alkoxy-5-trifluoromethyl-1-naphthoic acids are useful as pharmaceutical intermediates and that they can be prepared by the hydrolysis of the corresponding nitriles. It is also known that nitriles can generally be converted to acids via amide intermediates by acidic or basic hydrolysis. However, it has been found that the hydrolytic techniques conventionally employed in the hydrolysis of nitriles give unsatisfactory results when employed in the hydrolysis of 6-alkoxy-5-trifluoromethyl-1-cyanonaphthalenes. Hydrolysis of the nitrile group in such a compound under acidic conditions is accompanied by a competing hydrolysis of the trifluoromethyl group and by cleavage of the alkoxy group. Basic hydrolysis under normal conditions proceeds only to the formation and precipitation of an amide, and basic hydrolysis at higher temperatures is accompanied by attack of the trifluoromethyl group.

SUMMARY OF THE INVENTION

An object of this invention is to provide a novel process for preparing 6-alkoxy-5-trifluoromethyl-1-naphthoic acids.

Another object is to provide such a process wherein the acids are prepared in high yields from the corresponding nitriles.

These and other objects are attained by reacting a 6-alkoxy-5-trifluoromethyl-1-cyanonaphthalene with an aqueous alcoholic base under moderate pressure at a temperature of about 115°–130° C. so as to form a 6-alkoxy-5-trifluoromethyl-1-naphthoic acid.

DETAILED DESCRIPTION

The 6-alkoxy-5-trifluoromethyl-1-cyanonaphthalene that is hydrolyzed in the practice of the invention may be any such compound but is usually a 6-alkoxy-5-trifluoromethyl-1-cyanonaphthalene wherein the 6-substituent is an alkoxy group containing 1–20 carbons or such an alkoxy group bearing an inert substituent such as a phenyl, alkylphenyl, or alkoxyphenyl group, etc. The preferred 6-alkoxy-5-trifluoromethyl-1-cyanonaphthalenes are those wherein the alkoxy group is a lower alkoxy group (i.e., an alkoxy group containing 1–6 carbons), most preferably a straight-chain alkoxy group of 1–3 carbons or a branched-chain alkoxy group of 3 or 4 carbons, such as methoxy, ethoxy, 1-methylethoxy, butoxy, hexoxy, etc. A particularly preferred reactant is 6-methoxy-5-trifluoromethyl-1-cyanonaphthalene.

As taught by Ramachandran et al., the 6-alkoxy-5-trifluoromethyl-1-cyanonaphthalenes can be prepared by (1) cyanating a 6-alkoxytetralone to a 6-alkoxy-1-cyano-3,4-dihydronaphthalene, (2) aromatizing the product to a 6-alkoxy-1-cyanonaphthalene, (3) halogenating the 6-alkoxy-1-cyanonaphthalene to the corresponding 5-halo derivative, and (4) trifluoromethylating the 5-halo compound to replace the halo substituent with a trifluoromethyl group. This synthesis can be accomplished as follows:

(A) The 6-alkoxytetralone starting material, when not commercially available, can be prepared by known techniques, e.g., the techniques which can be learned directly or analogized from the teachings of Stork, *Journal of the American Chemical Society*, Vol. 69, pp. 576–579 (1947); Thomas et al., *Journal of the American Chemical Society*, Vol. 70, pp. 331–334 (1948); and Papa, *Journal of the American Chemical Society*, Vol. 71, pp. 3246–3247 (1949); as well as the references cited therein, the teachings of all of which are incorporated herein by reference.

(B) Cyanation of the 6-alkoxytetralone can be accomplished by conventional techniques or by the preferred technique of reacting the 6-alkoxytetralone with a cyanide, such as hydrogen cyanide or an alkali or alkaline earth metal cyanide, and a Lewis acid (most commonly aluminum chloride) at about 60°–120° C., suitably in the presence of a solvent and a phase transfer catalyst.

(C) Aromatization of the 6-alkoxy-1-cyano-3,4-dihydronaphthalene can be effected by conventional aromatization techniques, such as by heating it, preferably at reflux temperatures, in the presence of a palladium-on-carbon, platinum, nickel, or other dehydrogenation catalyst.

(D) Halogenation of the 6-alkoxy-1-cyanonaphthalene may be accomplished by known techniques, such as the techniques disclosed in March, *Advanced Organic Chemistry*, Second Edition, McGraw-Hill (New York), pp. 482–484, and the references cited therein, the teachings of all of which are incorporated herein by reference—the preferred halogenation techniques being the techniques known for the iodination or bromination of aromatic compounds.

(E) Trifluoromethylation may also be accomplished by known techniques, e.g., the trifluoromethylation technique of Matsui et al., *Chemistry Letters*, 1981, pp. 1719–1720.

The base with which the 6-alkoxy-5-trifluoromethyl-1-cyanonaphthalene is reacted may be any base strong enough to hydrolyze the nitrile group but is preferably an alkali or alkaline earth metal hydroxide, i.e., a lithium, sodium, potassium, rubidium, cesium, beryllium, magnesium, calcium, strontium, or barium hydroxide, and is most preferably sodium or potassium hydroxide. The amount employed should be at least an equivalent amount and is generally in the range of about 4–5 equivalents, based on the amount of 6-alkoxy-5-trifluoromethyl-1-cyanonaphthalene. However, larger amounts can be employed without any deleterious effect other than the obvious economic one.

The amount of water employed should be at least an equivalent amount and is ordinarily about 10–30 equivalents per equivalent of 6-alkoxy-5-trifluoromethyl-1-cyanonaphthalene. There is no actual maximum to the amount that may be used except in the sense that the volume amount of water in the reaction mixture should be less than the volume amount of alcohol.

The alcohol of the reaction mixture should be an alkanol containing 1–3 carbons, i.e., methanol, ethanol, n-propanol, or isopropanol, since the use of higher alcohols in the process does not appear to be conducive to the formation of 6-alkoxy-5-trifluoromethyl-1-naphthoic acids in high yields. The amount employed is usually such as to provide (a) at least one equivalent per equivalent of 6-alkoxy-5-trifluoromethyl-1-cyanonaphthalene, (b) a larger volume of alcohol than of water and (c) a concentration of 6-alkoxy-5-trifluoromethyl-1-cyanonaphthalene not higher than about 5%. It is generally preferred to use an amount of alcohol such that the weight/volume concentration of 6-alkoxy-5-trifluoromethyl-1-cyanonaphthalene in the alcohol/water mixture is about 0.5–5% and the alcohol/water volume ratio is in the range of about 1.1–15/1.

In the process of the invention, the ingredients can be combined in any order and are then heated at a temperature of about 115°–130° C., preferably about 120°–130° C., under moderate pressure so as to form a 6-alkoxy-5-trifluoromethyl-1-naphthoic acid. Temperatures lower than about 115° C. are generally undesirable because of the reaction's becoming more sluggish as the temperature is decreased; and temperatures higher than about 130° C., although operable, are apt to be undesirable because of the tendency for by-products to be formed as the temperature is increased. The same tendencies toward sluggishness or by-product formation are noted when the pressure is decreased or increased, and it has therefore been found most efficacious to conduct the reaction under a pressure of about 90–110 psi. The time required for the reaction varies with the particular conditions employed but is generally around 5–7 hours.

After completion of the reaction, the product may be subjected to further reactions to form derivatives, or it may be recovered by conventional means. It is an advantage of the invention that the process produces the desired product in high yield without the co-formation of substantial amounts of by-products.

The following example is given to illustrate the invention and is not intended as a limitation thereof.

EXAMPLE

A solution of 0.5 g of 6-methoxy-5-trifluoromethyl-1-cyanonaphthalene and 0.6 g of potassium hydroxide in 25 ml of a 20/5 mixture of methanol and water was charged into an autoclave, heated to 130° C. and stirred for 5–6 hours at an internal pressure of 90–100 psi. The reaction mixture was then cooled and worked up to provide a 98% recovered yield of 100% pure 6-methoxy-5-trifluoromethyl-1-naphthoic acid.

It is obvious that many variations can be made in the products and processes set forth above without departing from the spirit and scope of this invention.

What is claimed is:

1. A process which comprises reacting a 6-alkoxy-5-trifluoromethyl-1-cyanonaphthalene with an aqueous alcoholic base under moderate pressure at a temperature of about 115°–130° C. so as to form a 6-alkoxy-5-trifluoromethyl-1-naphthoic acid.

2. The process of claim 1 wherein the alkoxy substituent is an alkoxy group containing 1–6 carbons.

3. The process of claim 2 wherein the alkoxy group is methoxy.

4. The process of claim 1 wherein the base is an alkali or alkaline earth metal hydroxide.

5. The process of claim 4 wherein the base is an alkali metal hydroxide.

6. The process of claim 5 wherein the base is sodium or potassium hydroxide.

7. The process of claim 1 wherein the alcohol is an alkanol containing 1–3 carbons.

8. The process of claim 1 wherein the pressure is about 90–110 psi.

9. The process of claim 1 wherein a 6-alkoxy-5-trifluoromethyl-1-cyanonaphthalene is reacted with about 4–5 equivalents of an alkali metal hydroxide under a pressure of about 90–110 psi at a temperature of about 115°–130° C. in an amount of a water/alcohol mixture such as to provide a weight/volume concentration of about 0.5–5% of the 6-alkoxy-5-trifluoromethyl-1-cyanonaphthalene, the alcohol being an alkanol containing 1–3 carbons and being employed in an amount of such as to provide an alcohol/water volume ratio of about 1.1–15/1.

10. The process of claim 10 wherein the 6-alkoxy-5-trifluoromethyl-1-cyanonaphthalene is 6-methoxy-5-trifluoromethyl-1-cyanonaphthalene and the alkali metal hydroxide is sodium or potassium hydroxide.

* * * * *